(12) United States Patent
Palermo

(10) Patent No.: US 12,403,024 B2
(45) Date of Patent: Sep. 2, 2025

(54) VASCULAR AND AORTIC GRAFTS WITH TELESCOPING SHEATH AND DEPLOYMENT METHODS THEREOF

(71) Applicant: Aquedeon Medical, Inc., Sunnyvale, CA (US)

(72) Inventor: Thomas J. Palermo, San Jose, CA (US)

(73) Assignee: Aquedeon Medical, Inc., Sunnyvale, CA (US)

( * ) Notice: Subject to any disclaimer, the term of this patent is extended or adjusted under 35 U.S.C. 154(b) by 88 days.

(21) Appl. No.: 17/191,945

(22) Filed: Mar. 4, 2021

(65) Prior Publication Data

US 2021/0275336 A1     Sep. 9, 2021

Related U.S. Application Data

(60) Provisional application No. 62/984,898, filed on Mar. 4, 2020.

(51) Int. Cl.
*A61F 2/966* (2013.01)
*A61B 17/11* (2006.01)
(Continued)

(52) U.S. Cl.
CPC .............. *A61F 2/966* (2013.01); *A61B 17/11* (2013.01); *A61F 2/06* (2013.01); *A61F 2/9517* (2020.05);
(Continued)

(58) Field of Classification Search
CPC ........ A61F 2/9623; A61F 2/966; A61F 2/962; A61F 2/9661; A61F 2/97; A61F 2/9662;
(Continued)

(56) References Cited

U.S. PATENT DOCUMENTS 6,019,787 A     2/2000 Richard et al.
6,254,593 B1    7/2001 Wilson
(Continued)

FOREIGN PATENT DOCUMENTS

DE     102013160463    12/2014
EP       2111826 A1    10/2009
(Continued)

OTHER PUBLICATIONS

English translation of description for Ichiro et al. (Japan Patent No. JP2012065933) (Year: 2012).*

(Continued)

*Primary Examiner* — Kathleen S Holwerda
*Assistant Examiner* — Serenity A Miller
(74) *Attorney, Agent, or Firm* — Dergosits & Noah LLP; Todd A. Noah

(57) ABSTRACT

A vascular connector deployment tool may include a handle, an elongated mandrel extending distally from the handle, a vascular connector disposed coaxially about the mandrel, a retractable sheath assembly including an outer sheath telescopically deployed over an inner sheath and an actuator on the handle that is configured to selectively retract the outer sheath and the inner sheath relative to the mandrel. The sheath assembly is configured to constrain the vascular connector against the mandrel in an insertion profile. A distal transition between the outer sheath and the inner sheath visually indicates position of the vascular connector.

18 Claims, 5 Drawing Sheets

(51) Int. Cl.
    *A61F 2/06*         (2013.01)
    *A61F 2/95*         (2013.01)

(52) U.S. Cl.
    CPC ............... *A61B 2017/1107* (2013.01); *A61B 2017/1132* (2013.01); *A61F 2250/0097* (2013.01)

(58) Field of Classification Search
    CPC ...... A61F 2002/9665; A61F 2250/0097; A61F 2/9517; A61F 2/95; A61F 2/07; A61B 2017/1132; A61B 2017/1107; A61B 2017/1135; A61B 2017/1139
    See application file for complete search history.

(56) References Cited

U.S. PATENT DOCUMENTS

| | | | |
|---|---|---|---|
| 6,352,561 B1 | 3/2002 | Leopold et al. | |
| 7,879,904 B2 | 2/2011 | Zygmunt et al. | |
| 8,003,069 B2 | 8/2011 | Riebel et al. | |
| 8,641,752 B1 | 2/2014 | Holm et al. | |
| 8,778,006 B2 | 7/2014 | Fargahi et al. | |
| 8,904,764 B2 | 12/2014 | Baier et al. | |
| 9,192,500 B1 | 11/2015 | Longo et al. | |
| 9,763,819 B1 | 9/2017 | Sondreaal | |
| 9,972,933 B2 | 5/2018 | Kimura et al. | |
| 10,219,890 B2 | 3/2019 | Madjarov et al. | |
| 10,363,155 B2 | 7/2019 | Lesmeister et al. | |
| 11,684,466 B2 | 6/2023 | Varga | |
| 2003/0139805 A1 | 7/2003 | Holmberg et al. | |
| 2003/0199966 A1 | 10/2003 | Shiu et al. | |
| 2004/0044395 A1* | 3/2004 | Nelson .................. | A61F 2/966 623/1.13 |
| 2005/0027305 A1 | 2/2005 | Shiu et al. | |
| 2005/0033410 A1* | 2/2005 | Hogendijk ............. | A61F 2/07 623/1.15 |
| 2005/0080430 A1 | 4/2005 | Wright, Jr. et al. | |
| 2005/0182475 A1 | 8/2005 | Jen et al. | |
| 2006/0235501 A1* | 10/2006 | Igaki ...................... | A61F 2/962 623/1.11 |
| 2007/0100422 A1 | 5/2007 | Shumer et al. | |
| 2008/0097572 A1* | 4/2008 | Sheldon ................. | A61F 2/90 434/262 |
| 2008/0132993 A1 | 6/2008 | Rasmussen et al. | |
| 2008/0288042 A1* | 11/2008 | Purdy ..................... | A61F 2/95 623/1.11 |
| 2008/0294230 A1 | 11/2008 | Parker | |
| 2009/0125097 A1 | 5/2009 | Bruszewski et al. | |
| 2009/0254165 A1 | 10/2009 | Tabor et al. | |
| 2011/0288580 A1 | 11/2011 | Ginn et al. | |
| 2012/0065590 A1 | 3/2012 | Bierman et al. | |
| 2013/0226278 A1* | 8/2013 | Newell ................... | A61F 2/95 623/1.12 |
| 2013/0282103 A1 | 10/2013 | Madjarov et al. | |
| 2013/0310583 A1 | 11/2013 | Carlberg et al. | |
| 2015/0066131 A1* | 3/2015 | Luong .................... | A61M 25/008 623/1.11 |
| 2016/0022454 A1 | 1/2016 | Bonutti | |
| 2016/0151056 A1* | 6/2016 | Lederman .............. | A61B 17/11 606/213 |
| 2016/0270936 A1* | 9/2016 | Berra ...................... | A61M 39/06 |
| 2016/0287417 A1 | 10/2016 | Bhave et al. | |
| 2017/0252161 A1* | 9/2017 | Tran ........................ | A61F 2/966 |
| 2017/0290690 A1* | 10/2017 | Green ..................... | A61F 2/966 |
| 2018/0000619 A1 | 1/2018 | Longo et al. | |
| 2018/0085240 A1* | 3/2018 | Mower .................... | A61F 2/966 |
| 2018/0193043 A1 | 7/2018 | Marchand et al. | |
| 2019/0008631 A1* | 1/2019 | Stone ....................... | A61F 2/848 |
| 2019/0083101 A1 | 3/2019 | Broyles et al. | |
| 2019/0133748 A1* | 5/2019 | Torales ................... | A61B 17/11 |
| 2019/0151071 A1* | 5/2019 | Mogensen ............... | A61F 2/97 |
| 2019/0247213 A1 | 8/2019 | Lostetter | |
| 2019/0300218 A1 | 10/2019 | Patzer et al. | |
| 2020/0038213 A1* | 2/2020 | Bly ......................... | A61B 1/307 |

FOREIGN PATENT DOCUMENTS

| | | | |
|---|---|---|---|
| JP | 2001506902 A | 5/2001 | |
| JP | 2007007442 A | 1/2007 | |
| JP | 2006525074 A | 3/2007 | |
| JP | 2009523565 A | 6/2009 | |
| JP | 2012065933 A | 4/2012 | |
| JP | 2014501560 A | 6/2014 | |
| JP | 2015517850 A | 6/2015 | |
| JP | 2016137271 A | 10/2016 | |
| JP | 2018051259 A | 6/2018 | |
| JP | 2019528823 A | 12/2019 | |
| WO | 19980027894 | 7/1998 | |
| WO | 2007084762 A2 | 7/2007 | |
| WO | 2020010237 A1 | 1/2020 | |

OTHER PUBLICATIONS

International Search Report and Written Opinion in International Patent Publication No. PCT/US2021/020800, dated Jun. 15, 2021.
International Search Report and Written Opinion from related International Patent Application No. PCT/US2019/040566, dated Dec. 18, 2019.
International Search Report and Written Opinion from related International Patent Application No. PCT/US2019/068955, dated Aug. 19, 2020.
Search Report from related Japanese Patent Application No. 2021-521939, dated May 26, 2023.
Search Report from Japanese Patent Application No. 2022-518983 dated Aug. 23, 2023.
Search Report and Written Opinion from related International Patent Application No. PCT/US2022/37541, dated Nov. 4, 2022.
Notice of Reasons for Refusal from corresponding Japanese Patent Application No. 2022-552863 dated Apr. 15, 2025.

* cited by examiner

VASCULAR AND AORTIC GRAFTS WITH TELESCOPING SHEATH AND DEPLOYMENT METHODS THEREOF

RELATED APPLICATIONS

This patent application claims priority to U.S. Provisional Patent Application No. 62/984,898, filed Mar. 4, 2020, which is hereby incorporated by reference in its entirety and for all purposes.

FIELD OF THE PRESENT DISCLOSURE

The invention generally relates to vascular and aortic connectors, with particular regard to deployment tools and methods for such deploying such connectors.

BACKGROUND

The circulatory system includes the aorta and other large-diameter blood vessels, as well as smaller-diameter blood vessels and capillaries. Therapeutic interventions to replace or support diseased or otherwise compromised vessels may involve the use of synthetic grafts to maintain or restore patency of the affected vessel to perfuse downstream anatomy. Although disease and other conditions are known to affect all types of blood vessels, those affecting the aorta may be more serious and more likely to result in patient death, due to the volume and pressure of blood that is pumped through the aorta. Accordingly, the example discussed below is framed in the context of aortic grafts, but it should be appreciated that the techniques of this disclosure are applicable to other portions of a patient's vasculature.

Aortic aneurysm is a serious condition that can affect any segment of the aorta. An aortic aneurysm in the abdomen is referred to as an abdominal aortic aneurysm or AAA; an aortic aneurysm in the chest cavity is referred to as a thoracic aortic aneurysm or TAA, and an aneurysm in the chest cavity on the aortic arch may be referred to as an aortic arch aneurysm. Aortic aneurysms may result from different causes, such as untreated or severe hypertension, smoking, generic disease such as Marfan's syndrome, and degenerative dilation of the aortic wall. A thoracic aortic aneurysm results from weakening of the aortic wall, leading to localized dilatation, and is a life-threatening condition. Patients with thoracic aneurysms are often asymptomatic until the aneurysm expands. The most common presenting symptoms are pain and aortic rupture. A ruptured aneurysm can cause severe internal bleeding, which can rapidly lead to shock or death.

Patients with acute dissection typically present with pain and are classed as emergencies due to the risk of the dissection rupturing the wall of the aorta, affecting the integrity of the aortic valve and, through involvement of the origins of the coronary arteries, affecting perfusion of the myocardium. Typically, a dissection of the ascending aorta that extends into the aortic arch or that involves any of the arteries of the aortic arch requires surgical insertion of a graft to replace the diseased portion of the ascending aorta and additional grafts to reestablish blood flow to each artery stemming from the aortic branch where any dissection or disease is present. The grafts may be connected to the vasculature by expanding a connector from an insertion profile to a deployed profile to secure the graft to a vessel. The procedure may also involve inserting an additional stent that is dedicated to provide blood flow from the ascending aorta to vasculature distal of the descending aorta. Conditions affecting other portions of the patient's vasculature may also be treated in a similar manner.

Complex thoracic aortic disease encompasses acute (AAD) and chronic type A dissections (CAD), as well as aortic arch aneurysm with or without involvement of the ascending and descending aorta. Aortic dissection results from a tear in the inner layer of the wall of the aorta leading to blood entering and separating the layers of the wall. Acute aortic dissections are defined as those identified within the first 2 weeks after the initial tear, and chronic dissections are defined as those identified at times greater than 2 weeks. Aortic dissection is classified by its location and the extent of involvement of the thoracic aorta. Stanford Type A dissection affects the ascending aorta and may extend to the arch and descending thoracic aorta. Stanford Type B dissection does not affect the ascending aorta and typically involves the descending thoracic aorta, distal to the origin of the left subclavian artery. Approximately two-thirds of aortic dissections are Stanford Type A.

Treatment of complex thoracic aortic disease typically requires long and complicated open surgery. During such surgery, the patient is typically placed on a cardiopulmonary bypass pump, and the heart is stopped to allow the aorta to be clamped and operated upon. While the patient is on cardiopulmonary bypass, the patient generally is also chilled to a condition of hypothermia. The risk that the patient will not be able to survive the surgery is directly related to the duration of time that the patient spends on pump and under hypothermia.

Correspondingly, it would be desirable to provide tools and methods for deploying aortic connectors for aneurysm repair that facilitate and expedite their placement. Similarly, it would also be desirable to provide tools and methods that may be used for deploying connectors in other portions of a patient's vasculature. As will be detailed in the following materials, this disclosure satisfies these and other goals.

SUMMARY

The present disclosure is directed to a vascular connector deployment tool having a handle, an elongated mandrel extending distally from the handle, a vascular connector disposed coaxially about the mandrel, a retractable sheath assembly including an outer sheath telescopically deployed over an inner sheath, wherein the sheath assembly is configured to constrain the vascular connector against the mandrel in an insertion profile and wherein a distal transition between the outer sheath and the inner sheath visually indicates position of the vascular connector and an actuator on the handle that is configured to selectively retract the outer sheath and the inner sheath relative to the mandrel.

In one aspect, the inner sheath is visible through the outer sheath.

In one aspect, the outer sheath may be transparent.

In one aspect, the outer sheath may cover all of the vascular connector before retraction and the inner sheath may cover a predetermined amount of a proximal portion of the vascular connector before retraction. For example, the inner sheath may cover a proximal half of the vascular connector before retraction.

In one aspect, a distal end of the vascular connector may be visible through the outer sheath.

In one aspect, the actuator may be configured to initially retract only the outer sheath relative to the mandrel to expose a distal portion of the vascular connector and to subsequently retract both the outer sheath and the inner sheath relative to the mandrel to expose all of the vascular connector. The actuator may be a slider. The slider may be configured to initially engage only the outer sheath and to engage both the inner sheath and the outer sheath when reset. Alternatively, the slider may have a range of motion and may be configured to engage only the outer sheath over a first portion of the range of motion and to engage both the inner sheath and the outer sheath over a remaining portion of the range of motion.

In one aspect, the inner sheath may be transparent and a marker on a distal end of the inner sheath may be visible through the outer sheath. A stationary shoulder tube coaxially disposed over the mandrel and within the outer sheath and the inner sheath may abut a proximal end of the vascular connector. The shoulder tube may be visible through the outer sheath and the inner sheath.

In one aspect, the vascular connector may be a self-expanding connector that is able to maintain radial force at the temperature in a range of 22° C. to 37° C.

This disclosure also includes a method for implanting a vascular connector in a patient. The method may involve providing a vascular connector deployment tool including a handle, an elongated mandrel extending distally from the handle, a vascular connector disposed coaxially about the mandrel, a retractable sheath assembly including an outer sheath telescopically deployed over an inner sheath, wherein the sheath assembly constrains the vascular connector against the mandrel in an insertion profile, and an actuator on the handle that is configured to selectively retract the outer sheath and the inner sheath relative to the mandrel, positioning at least a distal portion of the vascular connector within a first lumen for conducting blood of the patient by visualizing a distal transition between the outer sheath and the inner sheath, manipulating the actuator to cause the outer sheath to retract relative to the mandrel and expose a distal portion of the vascular connector and securing the distal portion of the vascular connector within the first lumen by expansion of the portion of the vascular connector from the insertion profile.

In one aspect, positioning at least a distal portion of the vascular connector within the first lumen of the patient may involve advancing the deployment tool until a distal end of the inner sheath is adjacent an opening to the first lumen of the patient.

In one aspect, positioning at least a distal portion of the vascular connector within the first lumen of the patient may involve positioning one half of the vascular connector within the first lumen.

In one aspect, the method may also involve confirming stationarity of the deployment tool during retraction of the outer sheath by visualizing the inner sheath through the outer sheath.

In one aspect, a second lumen for conducting blood of the patient may be advanced coaxially over the deployment tool until an end of the second lumen is adjacent the opening of the first lumen, the actuator may be manipulated to cause the outer sheath and the inner sheath to retract relative to the mandrel and expose a remaining portion of the vascular connector and the remaining portion of the vascular connector may be secured within the second lumen by expansion of the portion of the vascular connector from the insertion profile. The first lumen may be a blood vessel and the second lumen may be a graft.

In one aspect, the deployment tool may have a shoulder tube that abuts the vascular connector such that the method also includes visualizing the shoulder tube through the outer sheath and the inner sheath to confirm placement of the vascular connector within the second lumen.

In one aspect, the vascular connector may be a self-expanding connector that is able to maintain radial force at the temperature in a range of 22° C. to 37° C.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. As used in this document, and as customarily used in the art, the word "substantially" and similar terms of approximation refer to normal variations in the dimensions and other properties of finished goods that result from manufacturing tolerances and other manufacturing imprecisions. Finally, as used in this specification and the appended claims, the singular forms "a," "an" and "the" include plural referents unless the content clearly dictates otherwise.

Figure 1:
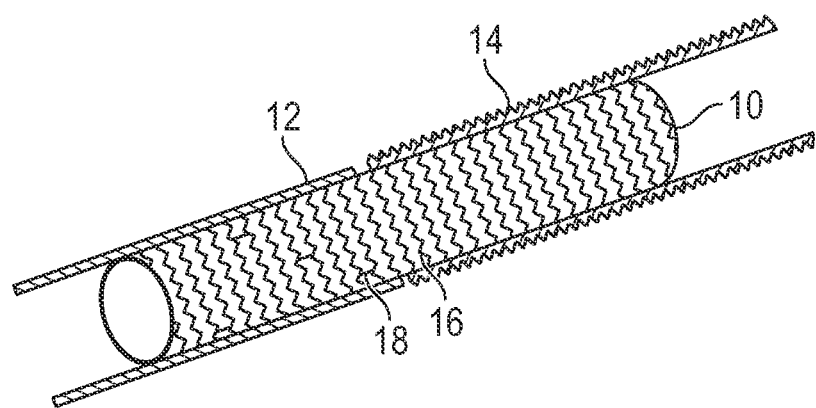
FIG. 1 schematically illustrates a vascular connector used to connect a blood vessel and a graft, according to an embodiment of the disclosure.

Referring to FIG. 1, a vascular connector 10 is shown that may be adapted for use in the aorta or other suitable locations in the patient's vasculature to help establish or restore fluid communication by joining blood vessel 12, such as one that may be dissected, to graft 14, such as a branch graft. Graft 14 may be fabricated from any suitable material or materials, such as but not limited to polytetrafluoroethylene (PTFE) or a polyester such as polyethylene terephthalate (PET), sometimes known as DACRON® brand polyester available from E. I. Du Pont De Nemours and Company of Wilmington, Delaware. The vascular connector 10 is expandable from a first insertion diameter to a second deployed diameter and may have any structure that allows for expansion from a first insertion diameter to a second deployed diameter and that holds vascular connector securely inside vessel 12 and graft 14 in the deployed state. As one example, vascular connector 10 may include a plurality of circumferentially extending hoops 16, similar in design to a stent. The hoops 16 may be longitudinally spaced apart; and if so, adjacent hoops 16 may be connected by one or more tie bars 18. Alternately, adjacent hoops 16 are not spaced apart, but instead abut or overlap one another. In such a configuration, such adjacent hoops 16 may be fixed to one another, such as by laser welding. The hoops 16 may be fabricated from metal or other material. Each hoop 16 may have a complex shape in which the hoop 16 is fabricated from a wire, or laser cut from a tube, or otherwise manufactured such that the hoop 16 has a complex shape, such as a zig-zag, repeating Z shape, tortuous curve, or other shape. Such a shape allows the hoop 16 to expand from an insertion diameter to a deployed diameter. The zig-zag pattern of at least one hoop 16 may be continuously curved, or may include straight segments connected by curved segments. In one embodiment, the zig-zag pattern of the hoops 16 may be as set forth in expired U.S. Pat. No. 4,580,568, which is incorporated herein by reference in its entirety. However, at least one hoop 16 may be configured differently.

In one embodiment, different hoops 16 may be fabricated from different materials. For example, at least one hoop 16 may be fabricated from superelastic material, such as nickel-titanium alloy, and at least one other hoop 16 may be fabricated from plastically-deformable material, such as 316L stainless steel. Adjacent hoops 16 may alternate between different materials, such that no hoop 16 is adjacent to a hoop 16 composed of the same material. In other embodiments, several hoops 16 composed of the same material may be grouped together, and at least one hoop 16 composed of a different material may be adjacent to that group. For example, a hoop 16 at an outer end of vascular connector 10 may be composed of stainless steel, and the remaining hoops 16 may be composed of superelastic material such as nickel-titanium alloy. By using hoops 16 fabricated from different materials, the vascular connector 10 takes advantage of the different properties of those different materials. For example, one or more hoops 16 fabricated from superelastic material are useful in self-expanding the vascular connector 10. One or more additional hoops 16 fabricated from a plastically-deformable material such as 316L stainless steel are useful for maintaining the lumen of vascular connector 10 open, because such material has greater resistance to hoop stress and is not susceptible to a return to a different crystal phase after expansion. In addition, such hoops 16 fabricated to be in structure configured to maintain its radial force at the temperature ranging from 22° C. to 37° C. Although the term "hoop" is used in this document, the hoops 16 need not be perfectly circular as viewed on end, and may have a different shape and curvature as suitable for a particular application. In some embodiments, the hoops 16 are substantially circular as viewed on end.

In one embodiment, the opposing ends of vascular connector 10 each expand to the same or similar diameters in the deployed state. In other embodiments, one end expands to a different diameter in the deployed state than the opposing end to allow joining a vessel 12 and graft 14 that have different diameters. The difference in diameter may be controlled by controlling the diameter of the hoops 16 in the respective ends, by providing a different mix of hoops 16 with different materials, or in any other suitable manner.

As noted above, vascular connector 10 may be used to join vessel 12 to graft 14 and it is correspondingly desirable to first deploy half the length of connector 10 into vessel 12, and then the other half of connector 10 within graft 14 to effectively connect the vessel 12 to the graft 14. Accurately deploying the proper amount of connector 10 into both the vessel 12 and graft 14 is advantageous since too much of the connector 10 being deployed in the vessel 12 risks the connection within the graft 14 while too little of the connector 10 being deployed in the vessel 12 risks connection within the vessel 12, and it should be appreciated that both scenarios can be catastrophic to the patient. Appropriate visualization greatly facilitates any open surgical procedure, so the techniques of this disclosure improve the ability to accurately assess the proper amount of connector 10 within the vessel 12 or branch graft 14 during the operation as discussed in detail below.

Figure 2:
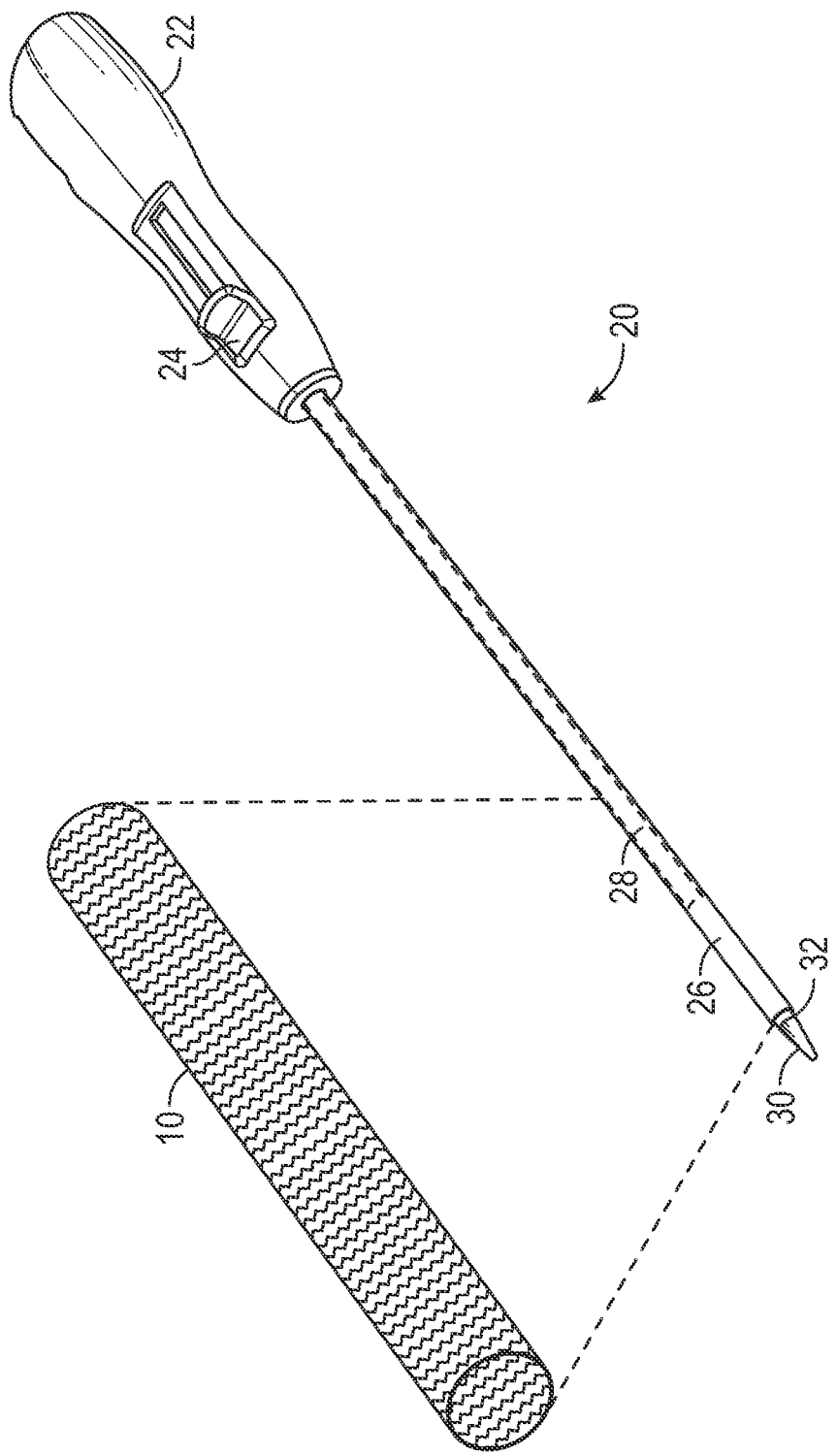
FIG. 2 schematically illustrates a deployment tool for positioning and placing a vascular connector, according to an embodiment of the disclosure.

Accordingly, vascular connector 10 or a connector having similar characteristics may be deployed using deployment tool 20 as schematically depicted in FIG. 2. Deployment tool 20 includes handle 22 having an actuator configured as slider 24 that is coupled to outer sheath 26 and inner sheath 28. At the distal end of deployment tool 20, is a blunt, atraumatic tip 30. As indicated, vascular connector 10 is wrapped around an internal mandrel 32 and compressed at least partially against the mandrel 32 by sheaths 26 and 28. Outer sheath 26 is telescopically disposed over inner sheath 28 and both are selectively retractable via actuation of slider 24. In one embodiment, a first actuation of slider 24 retracts only outer sheath 26 and a second actuation of slider 24 then retracts both outer sheath 26 and inner sheath 28 simultaneously as described in further detail below. Before retraction, outer sheath 26 covers the entire length of vascular connector 10 while inner sheath 28 covers a predetermined amount of the proximal portion of connector 10 determined based on the characteristics of the vascular connector 10 and the objectives of the procedure. As one example, one half of the overall connector length is covered by inner sheath 28 in the embodiment shown. To illustrate, inner sheath 28 may extend 3.5 cm over the proximal end of a 7 cm connector. Thus, the transition of inner sheath 28 and outer sheath 26 can be used to indicate the position of the vascular connector 10 to be deployed in the vessel 12 or the graft 14. The distances can be varied as warranted depending on the length of the connector 10 and the proportion desired to be covered. Sheaths 26 and 28 may be formed from suitable polymeric materials, such as nylon (polyamide), urethane, polypropylene, as well as polyamide co-polymers such as, for example, polyether block amides (PEBAX®), or others may be employed. Notably, outer sheath 26 is sufficiently translucent to allow at least the distal end of inner sheath 28 to be visualized through it (as indicated by the dashed lines), for example by using a substantially clear or transparent polymer. It should be recognized that clarity is relative and for the purposes of this disclosure, any difference in optical properties that enables inner sheath 28 to be visualized through outer sheath 26 may be used. As desired, inner sheath 28 may also employ any suitable optical property to facilitate visualization through outer sheath 26. For example, inner sheath 28 may have added coloration, such as a high visibility or high contrast characteristic. Alternatively, or in addition, inner sheath 28 may have relatively greater opacity than outer sheath 26. Further, outer sheath 26 may also allow visualization of connector 10, for example the distal portion not covered by inner sheath 28.

As will be appreciated, these characteristics of deployment tool 20 facilitate accurate placement of connector 10 within vessel 12 and graft 14. To the operator, the transition between the translucent outer sheath 26 and the visually distinguishable inner sheath 28 act as marker for a known location on connector 10. For example, in the shown embodiment in which inner sheath 28 covers one half of connector 10 before retraction provides identification of the mid-point of connector 10. Accordingly, this helps ensure that one half of the connector 10 is positioned within vessel 12, leaving the other half to secure graft 14. If different relative amounts of connector 10 are desired to be allocated to vessel 12 and graft 14 respectively, inner sheath 28 can be configured to cover the appropriate, predetermined amount of the connector 10. Furthermore, when deploying the distal portion of connector 10 by retracting outer sheath 26 alone, inner sheath 28 is visible and therefore allows continual confirmation that it remains stationary to indicate that the delivery system has not moved relative to the target landing area.

Figure 3:
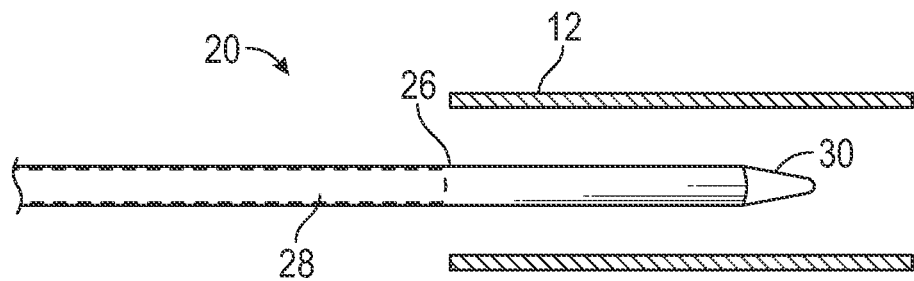
FIG. 3 schematically illustrates positioning a vascular connector within a blood vessel, according to an embodiment of the disclosure.
Figure 4:
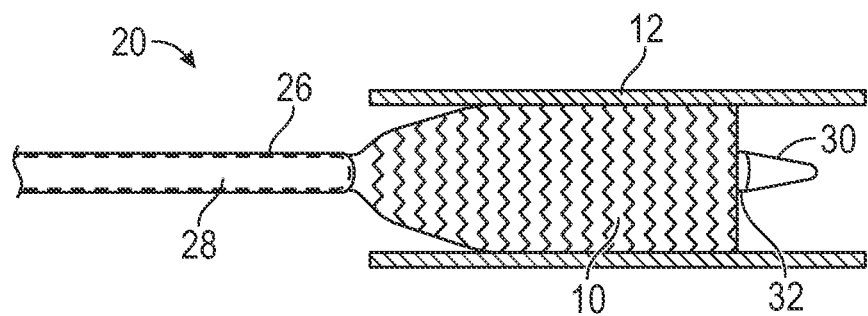
FIG. 4 schematically illustrates retracting an outer sheath of the deployment tool to allow expansion of a distal portion of the vascular connector to secure it within the blood vessel, according to an embodiment of the disclosure.
Figure 5:
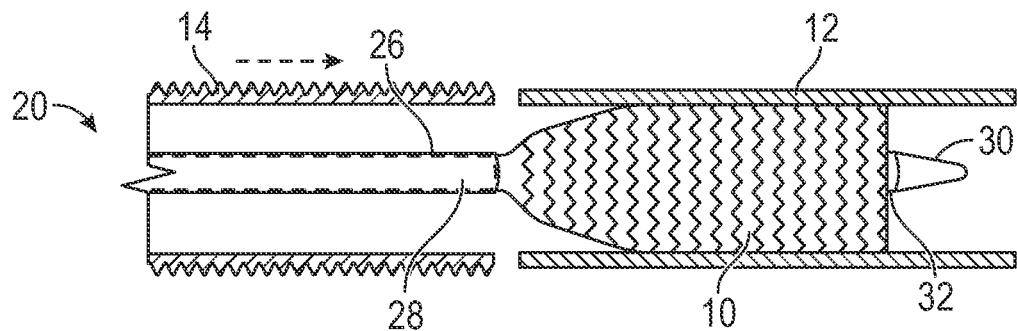
FIG. 5 schematically illustrates advancing a graft over the deployment tool to bring it into proximity with the blood vessel, according to an embodiment of the disclosure.
Figure 6:
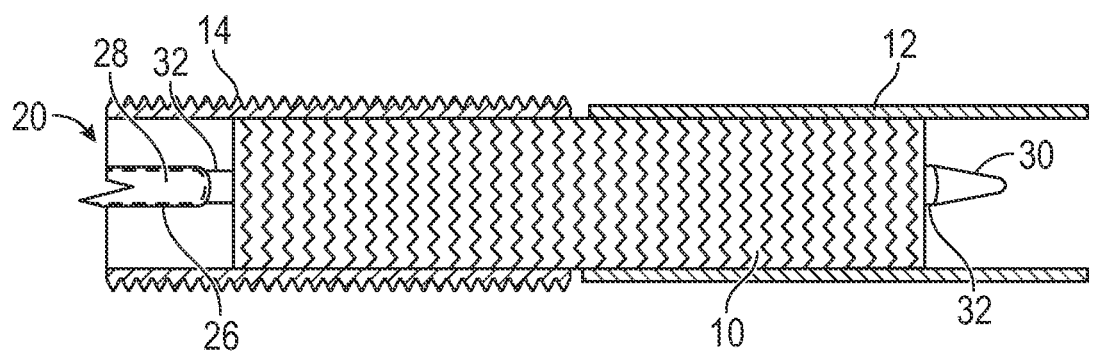
FIG. 6 schematically illustrates retracting the outer sheath and an inner sheath of the deployment tool to allow expansion of a remaining portion of the vascular connector to secure it within the graft, according to an embodiment of the disclosure.

As an illustration only and without limitation, FIGS. 3-6 schematically depict use of deployment tool 20 to connect vessel 12 to graft 14 with connector 10. As indicated in FIG. 3, deployment tool 20 may be advanced into vessel 12 until the distal end of inner sheath 28 is adjacent the opening of vessel 12. The distal end of inner sheath 28 can be visualized through the outer sheath 26 so that the vascular connector 10 can be easy to be positioned accurately in the vessel 12. Actuating slider 24 of deployment tool 20 causes retraction of outer sheath 26 alone, leaving inner sheath 28 stationary with respect to handle 22. As shown in FIG. 4, retraction of outer sheath 26 allows the distal portion of connector 10 that has now been exposed to expand from its insertion profile to its deployed profile to engage and secure vessel 12. Next, as indicated in FIG. 5, graft 14 may be advanced coaxially over deployment tool 20 until it is adjacent vessel 12, such as by abutting it or otherwise being in sufficient proximity. Now, subsequent actuation of slider 24 causes simultaneous retraction of both outer sheath 26 and inner sheath 28 to expose the remaining proximal portion of connector 10 so that it can expand from its insertion profile to its deployed profile to engage and secure graft 14. Deployment tool 20 can now be withdrawn proximally, leaving connector 12 in place to connect vessel 12 and graft 14. Any suitable mechanical implementation may be used to cause slider 24 to selectively retract outer sheath 26 or retract both outer sheath 26 and inner sheath 28. For example, slider 24 may engage only outer sheath 26 in an initial configuration. Resetting slider 24 after a first actuation may then engage inner sheath 28, so that subsequent actuation retracts both simultaneously. As another example, slider 24 may engage only outer sheath 26 over a first portion of its range of motion and then engage both outer sheath 26 and inner sheath 28 over the remainder of its range of motion. One of ordinary skill in the art will recognize that other techniques and mechanisms can be used to provide similar results. Further, the embodiment shown in FIGS. 3-6 is provided in the context of joining vessel 12 and graft 14 in an end-to-end configuration, however the techniques can also be applied to join any combination of vessels, grafts or other lumens that conduct the patient's blood and may also be used with an intra-vascular approach through an opening formed in a sidewall of a vessel, graft or other lumen.

Figure 7:
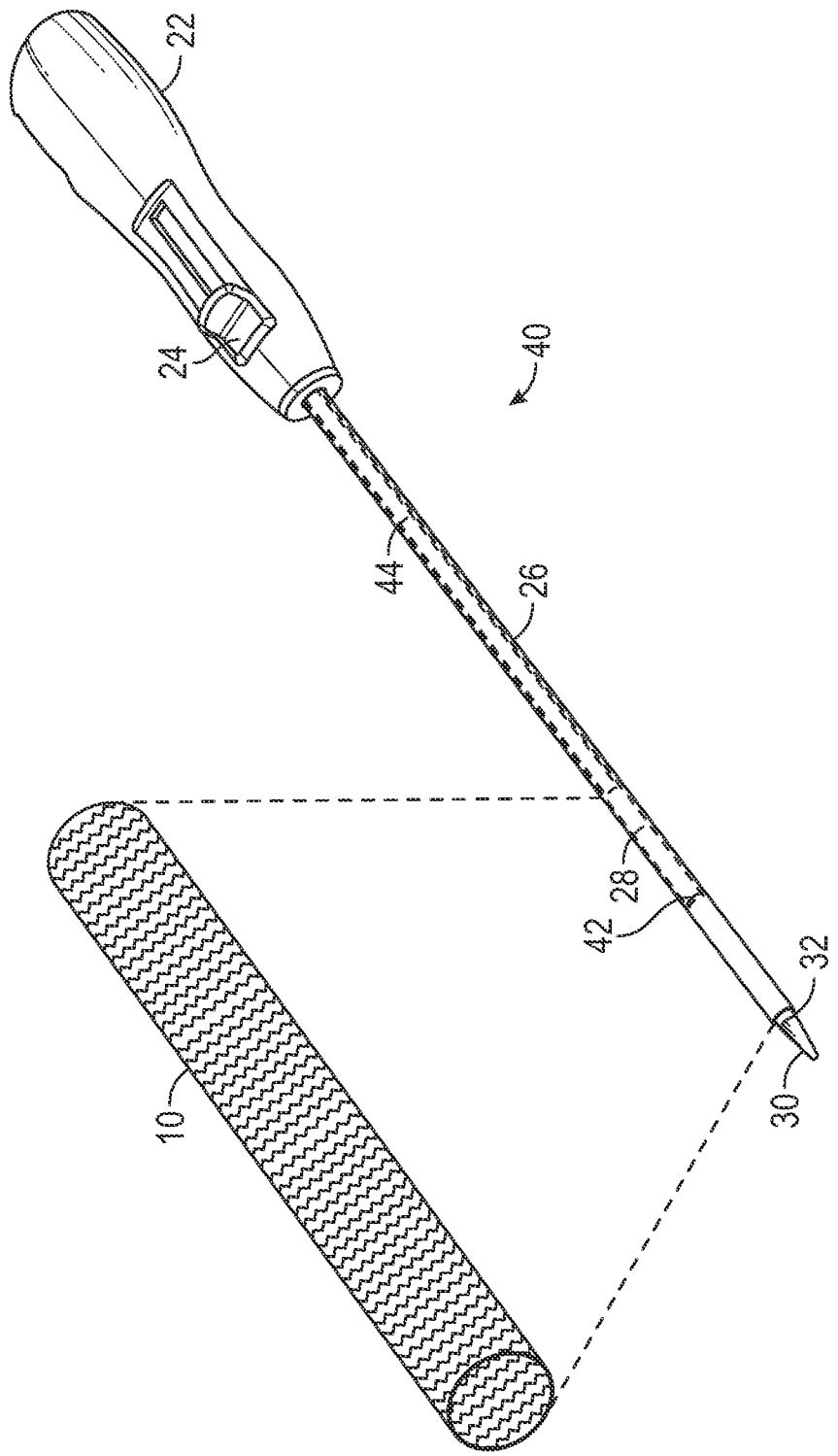
FIG. 7 schematically illustrates another deployment tool for positioning and placing a vascular connector, according to an embodiment of the disclosure.

Another embodiment of the techniques of this disclosure is schematically depicted in FIG. 7 in the context of deployment tool 40. Similar elements having similar functionality are indicated using the same reference numbers. As with the previous embodiment, deployment tool 40 also includes handle 22 having an actuator configured as slider 24 that is coupled to outer sheath 26 and inner sheath 28. At the distal end of deployment tool 20, is a blunt, atraumatic tip 30. As indicated, vascular connector 10 is wrapped around an internal mandrel 32 and compressed at least partially against the mandrel 32 by sheaths 26 and 28. Outer sheath 26 is telescopically disposed over inner sheath 28 and both are selectively retractable via actuation of slider 24. Again, a first actuation of slider 24 retracts only outer sheath 26 and a second actuation of slider 24 then retracts both outer sheath 26 and inner sheath 28 simultaneously. Also similarly, outer sheath 26 covers the entire length of vascular connector 10 before retraction and inner sheath 28 covers the desired predetermined amount of the proximal portion of connector 10 as discussed above. In this embodiment, both outer sheath 26 and inner sheath 28 are clear or otherwise sufficiently transparent and the transition between the outer sheath 26 and inner sheath 28 is visually indicated by circumferential ring 42 or any other suitable marker that can be visualized through outer sheath 26. Deployment tool 40 also features a stationary shoulder tube 44 that abuts the proximal end of connector 10 and which is colored or otherwise visible through both outer sheath 26 and inner sheath 28. Shoulder tube 44 functions to resist proximal movement of connector 10 during retraction of outer sheath 26 and inner sheath 28. Further, the visibility of shoulder tube 44 also functions as a ready visual indicator of the location of the proximal end of vascular connector 10. During use, this indication may be used to confirm that the proximal portion of connector 10 is wholly within graft 14 for example and does not extend out of the opening through which deployment tool 40 is advanced. As will be appreciated, deployment tool 40 may be used to position and deliver connector 10 to connect blood carrying lumens of a patient as described above.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the claims and their legal equivalents.

What is claimed is:

1. A vascular connector deployment tool, comprising:
a handle;
an elongated mandrel extending distally from the handle, the mandrel having a proximal end coupled to the handle, a distal end and an outer surface;
a vascular connector having a proximal circumferential portion and a distal circumferential portion disposed over a portion of the mandrel distal end, the vascular connector being expandable from a first insertion diameter to a second deployed diameter and has a structure that allows for expansion from the first insertion diameter to the second deployed diameter, the structure being configured to hold the vascular connector securely inside a blood vessel and a graft in the deployed state;
a retractable sheath assembly including a translucent retractable outer sheath telescopically deployed over a retractable inner sheath that is visible through the outer sheath, wherein the inner and outer sheaths of the retractable sheath assembly are configured to constrain the vascular connector against the outer surface of the mandrel in an insertion profile and wherein a distal transition between the outer sheath and the inner sheath visually indicates position of the vascular connector; and
a single actuator on the handle, the single actuator being configured as a slider having a longitudinal range of motion in a slot on the handle, the slider being mechanically coupled to both the outer sheath and the inner sheath to initially retract only the outer sheath relative to the mandrel to expose the distal circumferential portion of the vascular connector and cause the distal circumferential portion to expand from the first insertion diameter to the second deployed diameter, and to subsequently retract the outer sheath and the inner sheath relative to the mandrel to expose the proximal circumferential portion of the vascular connector and cause the proximal circumferential portion to expand from the first insertion diameter to the second deployed diameter.

2. The vascular connector deployment tool of claim 1, wherein the outer sheath covers all of the vascular connector before retraction, and wherein the inner sheath covers a predetermined amount of the proximal circumferential portion of the vascular connector before retraction.

3. The vascular connector deployment tool of claim 2, wherein the inner sheath covers a proximal half of the vascular connector before retraction.

4. The vascular connector deployment tool of claim 3, wherein a distal end of the vascular connector is visible through the outer sheath.

5. The vascular connector deployment tool of claim 1, wherein, upon a first actuation of the slider, the slider is configured to initially engage only the outer sheath and when the slider is reset after the first actuation, the slider then engages the inner sheath such that subsequent actuation retracts both the outer sheath and inner sheath simultaneously.

6. The vascular connector deployment tool of claim 1, wherein the slider has a range of motion and is configured to engage only the outer sheath over a first portion of the range of motion and to engage both the inner sheath and the outer sheath over a remaining portion of the range of motion.

7. The vascular connector deployment tool of claim 1, wherein the inner sheath is transparent and a marker on a distal end of the inner sheath is visible through the outer sheath.

8. The vascular connector deployment tool of claim 7, further comprising a stationary shoulder tube coaxially disposed over the mandrel and within the outer sheath and the inner sheath that abuts a proximal end of the vascular connector.

9. The vascular connector deployment tool of claim 8, wherein the shoulder tube is visible through the outer sheath and the inner sheath.

10. The vascular connector deployment tool of claim 1, wherein the vascular connector is self-expanding connector and is able to maintain radial force at the temperature in a range of 22° C. to 37° C.

11. A method for implanting a vascular connector in a patient, comprising:
providing a vascular connector deployment tool including a handle, an elongated mandrel extending distally from the handle, the mandrel having a proximal end coupled to the handle, a distal end and an outer surface having a circumference, a vascular connector having a proximal circumferential portion and a distal circumferential portion disposed coaxially around the circumference of the mandrel outer surface at the distal end, the vascular connector being expandable from a first insertion diameter to a second deployed diameter and has a structure that allows for expansion from the first insertion diameter to the second deployed diameter, the structure being configured to hold the vascular connector securely inside a first lumen and a second lumen in the deployed state, a retractable sheath assembly including a translucent retractable outer sheath telescopically deployed over a retractable inner sheath that is visible through the outer sheath, wherein the retractable sheath assembly constrains the vascular connector against the outer surface of the mandrel in an insertion profile, and a single actuator on the handle, the single actuator being configured as a slider having a longitudinal range of motion in a slot on the handle, the slider being mechanically coupled to both the outer sheath and the inner sheath to initially retract only the outer sheath relative to the mandrel to expose the distal circumferential portion of the vascular connector and cause the distal circumferential portion to expand from the first insertion diameter to the second deployed diameter, and to subsequently retract the outer sheath and the inner sheath relative to the mandrel to expose the proximal circumferential portion of the vascular connector and cause the proximal circumferential portion to expand from the first insertion diameter to the second deployed diameter;

positioning at least the distal circumferential portion of the vascular connector within the first lumen for conducting blood of the patient by visualizing a distal transition between the outer sheath and the inner sheath;

manipulating the actuator to cause the outer sheath to retract relative to the mandrel and expose the circumferential distal portion of the vascular connector; and securing the distal portion of the vascular connector within the first lumen by expansion of the circumferential distal portion of the vascular connector from the insertion profile.

12. The method of claim 11, wherein positioning at least the distal portion of the vascular connector within the first lumen of the patient comprises advancing the deployment tool until a distal end of the inner sheath is adjacent an opening to the first lumen of the patient.

13. The method of claim 11, wherein positioning at least the distal portion of the vascular connector within the first lumen of the patient comprises positioning one half of the vascular connector within the first lumen.

14. The method of claim 11, further comprising confirming the deployment tool remains stationary during retraction of the outer sheath by visualizing the inner sheath through the outer sheath.

15. The method of claim 11, further comprising:

advancing the second lumen for conducting blood of the patient coaxially over the deployment tool until an end of the second lumen is adjacent the opening of the first lumen;

manipulating the actuator to cause the outer sheath and the inner sheath to retract relative to the mandrel and expose the proximal circumferential portion of the vascular connector; and securing the proximal circumferential portion of the vascular connector within the second lumen by expansion of the proximal circumferential portion of the vascular connector from the insertion profile.

16. The method of claim 15, wherein the first lumen is a blood vessel and the second lumen is a graft.

17. The method of claim 15, wherein the deployment tool has a shoulder tube that abuts the vascular connector and further comprising visualizing the shoulder tube through the outer sheath and the inner sheath to confirm placement of the vascular connector within the second lumen.

18. The method of claim 11, wherein the vascular connector is self-expanding connector and is able to maintain radial force at the temperature in a range of 22° C. to 37° C.

* * * * *